United States Patent [19]

Plummer et al.

[11] 4,339,457
[45] Jul. 13, 1982

[54] 3-(PYRROL-1-YL)PHENYLMETHYL ESTERS AND INTERMEDIATES

[75] Inventors: Ernest L. Plummer, North Tonawanda, N.Y.; Raymond M. Palmere, West Orange, N.J.

[73] Assignee: FMC Corporation, Philadelphia, Pa.

[21] Appl. No.: 198,409

[22] Filed: Oct. 20, 1980

[51] Int. Cl.$^3$ .............. C07D 207/327; A01N 43/36
[52] U.S. Cl. ................................. 424/274; 548/563
[58] Field of Search .............. 260/326.41, 326.5 R; 424/274

[56] References Cited

U.S. PATENT DOCUMENTS

| | | | |
|---|---|---|---|
| 3,631,069 | 12/1971 | Renner et al. | 260/326.41 |
| 3,850,977 | 11/1974 | Nabnshigo et al. | 260/468 H |
| 3,928,380 | 12/1975 | Bell et al. | 260/326.9 |
| 4,024,163 | 5/1977 | Elliott et al. | 260/326 A |
| 4,130,657 | 12/1978 | Plummer | 560/124 |
| 4,151,293 | 4/1979 | Stein | 548/378 |
| 4,214,004 | 7/1980 | Plummer | 560/124 |
| 4,238,505 | 12/1980 | Engel | 560/124 |

FOREIGN PATENT DOCUMENTS 3336 8/1979 European Pat. Off. .
1263940 2/1972 United Kingdom .

OTHER PUBLICATIONS

Khaden et al.; J. Het. Chem. vol. 9, pp. 1413–1417 (1972).
Grammaticakis, Chem. Abs. vol. 75:35577u (1971).
Wibaut et al.; Chem. Abs. 38:2337$^6$ (1943).
Holan et al.; Nature vol. 272, pp. 734–736 (1978).
Stefancich et al.; J. Het. Chem. vol. 16, pp. 1443–1447 (1979).
Vomero et al.; Chem. Abs. vol. 85:192525z (1976).

Primary Examiner—Mary C. Lee
Attorney, Agent, or Firm—Robert L. Andersen; H. Robinson Ertelt

[57] ABSTRACT 3-(Pyrrol-1-yl)phenylmethyl esters and intermediates having the general formula

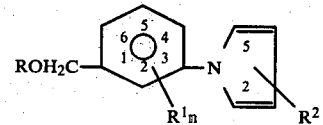

the use of the esters as pesticides, compositions thereof and a process for preparation are disclosed and exemplified.

12 Claims, No Drawings

3-(PYRROL-1-YL)PHENYLMETHYL ESTERS AND INTERMEDIATES

The present invention relates to novel carboxylic acid esters, compositions of such esters, use for control of insects and acarids, and novel intermediates for the preparation of those esters. More particularly, the invention relates to cyclopropanecarboxylate and related esters of the pyrethroid type in which the alcohol component of the molecule is based on a 3-(pyrrol-1-yl)phenylmethanol.

Pyrethrins, naturally occurring extracts of chrysanthemum flowers, have long been of interest as insecticides. Since elucidation of the structures of these compounds, synthesis efforts have been directed toward preparation of related compounds having enhanced insecticidal activity and improved stability toward air and light. Since a prerequisite for insecticidal activity of pyrethroids is the presence in one molecule of an appropriate acid moiety and an appropriate alcohol moiety, research in the art has been directed toward novel acid and/or alcohol radicals. Noteworthy advances in the area of alcohol research were the discovery of 5-benzyl-3-furylmethyl alcohol, then the more photostable 3-phenoxybenzyl alcohol (see *Synthetic Pyrethroids*, ACS Symposium Series, No. 42, M. Elliott, Ed., American Chemical Society, Washington, D.C. 1977, Chapter 1). These two alcohols are representative of a common structural type in which two ring systems are connected to each other by an —O—, —S—, —CH$_2$—, or —CO— linkage, a relationship previously thought necessary for high insecticidal efficacy.

A more recent advance in alcohol research was the discovery by Plummer that the connecting unit —O— between the two phenyl rings in 3-phenoxybenzyl alcohol was not essential for high insecticidal activity. In U.S. Pat. No. 4,130,657, Plummer discloses various [1,1'-biphenyl]-3-ylmethyl 3-(2,2-dihaloethenyl)-2,2-dimethylcyclopropanecarboxylates as potent insecticides and acaricides.

The present invention provides a new series of novel benzyl alcohols having an optionally substituted pyrrole ring attached at the 1 position, i.e. by the nitrogen atom, directly to the phenyl ring of the benzyl group. The novel alcohols produce highly potent insecticidal esters when chemically combined with an appropriate acid.

The definitions which follow are applicable throughout the specification and claims of this application except where a different meaning is clearly indicated. The term "lower" as applied to a hydrocarbyl group, as in "lower alkyl" or "lower alkoxy", means a straight or branched chain hydrocarbyl group or having 1 to 4 carbon atoms, preferably 1 to 2 carbon atoms. The term "halo" or "halogen" means bromine, chlorine, fluorine or iodine, preferably bromine, fluorine, or chlorine.

The novel alcohols and insecticidal esters of this invention have the general formula I

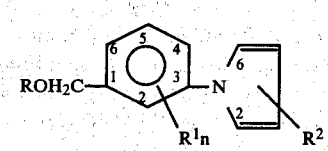

wherein R$^1$ is halogen or lower alkyl, n is 0, 1, or 2, R$^2$ is hydrogen or 2,5-dimethyl, and R is hydrogen or a pyrethroid acid residue. Typical pyrethroid acid residues include groups such as 2,2,3,3-tetramethylcyclopropylcarbonyl, 1-(4-chlorophenyl)-2-methylpropyl-1-carbonyl, 1-(4-ethoxyphenyl)-2,2-dichlorocyclopropylcarbonyl, or a cyclopropanecarboxylic acid residue of the formula

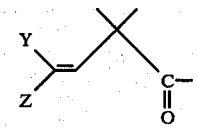

II wherein Y and Z are independently halogen, lower alkyl or perhaloalkyl of 1 or 2 carbon atoms or are joined to form a cyclopentylidene ring. Particularly interesting are the insecticidal esters of formula II in which one of Y and Z is a halogen, preferably bromine or chlorine, and the other is halogen or perhaloalkyl of 1 or 2 carbon atoms, preferably trifluoromethyl, when chemically combined in molecules containing the novel alcohols of this invention.

Novel alcohol intermediates for these pyrethroids are those of formula I in which R is hydrogen. Insecticides and intermediates of particular interest are those in which R$^1$ is hydrogen when n is 0, or is halogen or lower alkyl at the 2 position of the phenyl ring when n is 1, or is halogen or lower alkyl at the 2 and 6 positions of the phenyl ring when n is 2.

The insecticides of this invention having the acid residue of formula II have cis and trans isomeric forms; the carboxy and the substituted vinyl groups at the 1 and 3 positions of the cyclopropane ring are either cis or trans with respect to each other. Preparation of these compounds will usually yield a mixture of the cis and trans isomers, designated cis,trans, in which the ratio of cis to trans may vary over a wide range. For purposes of this application the designation cis and trans are assigned in accordance with P. E. Burt, et al., Pestic. Sci., 5 791–799 (1974). Certain compounds of this invention may also exist as E or Z isomers or as mixtures of E and Z isomers, designated EZ, depending upon the spatial relationship of substituents on the α-carbon of the vinyl group to those on the β-carbon of the vinyl group.

In the cyclopropanecarboxylate art it is known there may be substantial differences in the level of insecticidal activity of the cis and trans isomers. In general, as between the cis and trans isomers of a given cyclopropanecarboxylate, the cis isomer is usually the more active, is also more active than the cis,trans mixture. Similar differences in activity may also occur with respect to the E and Z isomers.

Unless a contrary intent is specifically expressed, this invention embodies and includes both cis and trans isomeric forms of the claimed compounds as well as mixtures thereof wherein the cis to trans ratio is within the range of 0:100 to 100:0. Similarly, the individual E and Z isomers, as well as the mixtures, are contemplated by and within the scope of the invention. The various enantiomers of the claimed compounds and mixtures of them are also included within the scope of the invention.

The following examples illustrate several methods for preparation of the intermediates of this invention.

EXAMPLE 1

Synthesis of 3-(pyrrol-1-yl)phenylmethanol as an intermediate (Route I)

Step A Synthesis of ethyl 3-(pyrrol-1-yl)benzoate

To 60 ml of stirred glacial acetic acid was added 25.0 grams (0.15 mole) of ethyl 3-aminobenzoate. The mixture was stirred for two minutes and 19.6 grams (0.15 mole) of 2,5-dimethoxytetrahydrofuran was added during a five minute period. Upon complete addition the red solution was heated under reflux for 1.5 hours. The acetic acid solvent was removed by distillation. Higher boiling volatiles were also removed by distillation, under reduced pressure (80°–110° C./55 2 mm). Pure ethyl 3-(pyrrol-1-yl)benzoate was obtained by distillation under reduced pressure; bp 143°–145° C./2 mm. The product solidified on standing; mp 62°–64° C. The yield was 25.4 grams of white solid.

The nmr and the ir spectra were consistent with the proposed structure.

Analysis calc'd for $C_{13}H_{13}NO_2$: C, 72.54; H, 6.09; N, 6.51; Found: C, 72.99; H, 6.20; N, 6.45.

Step B Synthesis of 3-(pyrrol-1-yl)phenylmethanol

To a stirred mixture of 4.8 grams of lithium aluminum hydride in 150 ml of dry diethyl ether was added dropwise 23.2 grams (0.108 mole) of ethyl 3-(pyrrol-1-yl)benzoate in 160 ml of dry diethyl ether. The complete addition required 45 minutes. After this time the reaction mixture was heated under reflux for 45 minutes then allowed to cool to ambient temperature where it stood for 16 hours. The excess lithium aluminum hydride was decomposed by the careful addition of 20 ml of 50% (v/v) water-tetrahydrofuran. The addition required 20 minutes as the reaction mixture temperature was kept below 25° C. The reaction mixture was poured into 300 ml of water and the diethyl ether layer separated. The aqueous layer was extracted with three portions of 200 ml each of diethyl ether. The combined ether layers were washed with water and dried with magnesium sulfate. The mixture was filtered and the filtrate concentrated under reduced pressure to give 20.9 grams of 3-(pyrrol-1-yl)phenylmethanol; mp 64°–67° C. The ir spectrum was consistent with the proposed structure.

EXAMPLE 2

Synthesis of 2-methyl-3-(pyrrol-1-yl)phenylmethanol as an intermediate (Route II)

Step A Synthesis of 1-(3-chloro-2-methylphenyl)pyrrole

This compound was prepared in the manner of Example 1, Step A using 80.3 grams (0.567 mole) of 3-chloro-2-methylaniline, 75.0 grams (0.567 mole) of 2,5-dimethoxytetrahydrofuran in 120 ml of glacial acetic acid. The yield of 1-(3-chloro-2-methylphenyl)pyrrole was 98.4 grams as an oil.

The nmr and the ir spectra were consistent with the proposed structure.

Analysis calc'd for $C_{11}H_{10}ClN$: C, 68.94; H, 5.25; Found: C, 68.98; H, 5.45.

Step B Synthesis of 2-methyl-3-(pyrrol-1-yl)benzoic acid

A sample of 1.27 grams (0.052 mole) of magnesium metal was placed in a Morton Flask. The flask and contents were flame-dried under a nitrogen atmosphere. After the flask and contents were cooled, 10.0 grams (0.052 mole) of 1-(3-chloro-2-methylphenyl)pyrrole, a few crystals of iodine, and 20 ml of tetrahydrofuran were added; followed by three drops of methyl iodide. The reaction was commenced by the addition of an external Grignard Reagent of magnesium, methyl iodide and tetrahydrofuran. Once started, the reaction warmed the stirred reaction mixture to reflux. A precipitate appeared and was dissipated by the addition of 20 ml of tetrahydrofuran. The reaction mixture was heated under reflux for 22.5 hours. After this time the reaction mixture was cooled and crushed dry ice ($CO_2$) was added until a thick slurry formed. An additional 20 ml of tetrahydrofuran was added and the thick slurry was reformed by the addition of more dry ice. The reaction mixture was stirred while being allowed to warm to ambient temperature. After the reaction mixture had warmed an aqueous solution saturated with ammonium chloride was added until a solid precipitate appeared. Upon complete addition the reaction mixture was stirred for 2.5 hours then 150 ml of diethyl ether was added. The mixture was filtered through a small amount of magnesium sulfate. The filtrate was concentrated under reduced pressure to a residual oil. The residual oil was dissolved in diethyl ether and extracted with three portions of 200 ml each of aqueous 2 N sodium hydroxide. The combined basic layers were washed with 200 ml of diethyl ether and acidified to pH=1 with concentrated hydrochloric acid. A solid precipitate formed. The mixture was cooled and extracted with four portions of 200 ml each of diethyl ether. The combined extracts were dried with magnesium sulfate and filtered. The filtrate was concentrated under reduced pressure to give 9.8 grams of 2-methyl-3-(pyrrol-1-yl)benzoic acid; mp 146°–148.5° C.

The nmr and the ir spectra were consistent with the proposed structure.

Analysis calc'd for $C_{12}H_{11}NO_2$: C, 71.63; H, 5.51; Found: C, 71.51; H, 5.51.

Step C Synthesis of 2-methyl-3-(pyrrol-1-yl)phenylmethanol

To a stirred solution of 7.5 grams (0.037 mole) of 2-methyl-3-(pyrrol-1-yl)benzoic acid in 125 ml of tetrahydrofuran was added dropwise 4.8 grams (0.056 mole) of a borane-tetrahydrofuran complex. The addition required 30 minutes. Upon complete addition the reaction mixture was heated under reflux for 2.5 hours then cooled slowly. To the cooled reaction mixture was carefully added 150 ml of diethyl ether previously saturated with water, followed by 50 ml of water. The mixture was poured into a separatory funnel and washed with 100 ml of aqueous 2 N sodium hydroxide. The organic layer was dried with magnesium sulfate and filtered. The filtrate was concentrated under reduced pressure to give 6.8 grams of 2-methyl-3-(pyrrol-1-yl)phenylmethanol as an oil.

The nmr and the ir spectra were consistent with the proposed structure.

EXAMPLE 3

Synthesis of
3-(2,5-dimethylpyrrol-1-yl)phenylmethanol as an
intermediate (Route III)

Step A Synthesis of 3-(2,5-dimethylpyrrol-1-yl)benzoic acid

In a reaction vessel equipped with a Dean-Stark trap was placed 13.7 grams (0.10 mole) of 3-aminobenzoic acid, 11.4 grams (0.10 mole) of acetonylacetone, 0.10 gram of p-toluenesulfonic acid and 150 ml of toluene. The stirred reaction mixture was heated under reflux for 15.5 hours during which time the theoretical amount of by-product water was collected in the Dean-Stark trap. The reaction mixture was cooled and placed in a separatory funnel where it was washed with two portions of 50 ml each of aqueous 2N sodium hydroxide. The combined base washes were backwashed with 50 ml of toluene then acidified with aqueous 2 N hydrochloric acid. A solid precipitate was collected by filtration and recrystallized from heptane to give 19.3 grams of 3-(2,5-dimethylpyrrol-1-yl)benzoic acid; mp 148°–150° C.

The nmr and the ir spectra were consistent with the proposed structure.

Analysis calc'd for $C_{13}H_{13}NO_2$: C, 72.54; H, 6.09; Found: C, 72.54; H, 5.87.

Step B Synthesis of
3-(2,5-dimethylpyrrol-1-yl)phenylmethanol

This compound was prepared in the manner of Example 2, Step C using 16.6 grams (0.077 mole) of 3-(2,5-dimethylpyrrol-1-yl)benzoic acid and 100 ml (0.10 mole) of borane-tetrahydrofuran complex in 250 ml of tetrahydrofuran. The yield of 3-(2,5-dimethylpyrrol-1-yl)phenylmethanol was 15.1 grams. The nmr and the ir spectra were consistent with the proposed structure.

Analysis calc'd for $C_{13}H_{15}NO$: C, 77.58; H, 7.51; Found: C, 74.85; H, 6.92.

EXAMPLE 4

Synthesis of
2-methyl-3-(2,5-dimethylpyrrol-1-yl)phenylmethanol as
an intermediate (Route IV)

Step A Synthesis of
1-(3-chloro-2-methylphenyl)-2,5-dimethylpyrrole

This compound was prepared in the manner of Example 3, Step A using 50.0 grams (0.353 mole) of 3-chloro-2-methylaniline, 40.3 grams (0.353 mole) of acetonylacetone and 0.5 gram of p-toluenesulfonic acid in 300 ml of toluene. The yield of 1-(3-chloro-2-methylphenyl)-2,5-dimethylpyrrole was 77.6 grams; bp 90±3° C./0.05 mm.

The nmr and the ir spectra were consistent with the proposed structure.

Analysis calc'd for $C_{13}H_{14}ClN$: C, 71.07; H, 6.42; Found: C, 70.08; H, 6.30.

Step B Synthesis of
2-methyl-3-(2,5-dimethylpyrrol-1-yl)benzoic acid

This compound was prepared in the manner of Example 2, Step B using 25.0 grams (0.114 mole) of 1-(3-chloro-2-methylphenyl)-2,5-dimethylpyrrole, 2.8 grams (0.114 mole) of magnesium metal, a catalytic amount of methyl iodide and a catalytic amount of iodine crystal in 50 ml of tetrahydrofuran. The yield of 2-methyl-3-(2,5-dimethylpyrrol-1-yl)benzoic acid was 20.7 grams; mp 142°–143° C.

The nmr and the ir spectra were consistent with the proposed structure.

Analysis calc'd for $C_{14}H_{15}NO_2$: C, 73.35; H, 6.59; Found: C, 73.58; H, 7.09.

Step C Synthesis of
2-methyl-3-(2,5-dimethylpyrrol-1-yl)phenylmethanol

This compound was prepared in the manner of Example 2, Step C using 18.2 grams (0.079 mole) of 2-methyl-3-(2,5-dimethylpyrrol-1-yl)benzoic acid, and 10.2 grams of boranetetrahydrofuran complex in 200 ml of tetrahydrofuran. The yield of 2-methyl-3-(2,5-dimethylpyrrol-1-yl)phenylmethanol was 5.4 grams; bp 145° C./0.05 mm.

The nmr and the ir spectra were consistent with the proposed structure.

Analysis calc'd for $C_{14}H_{17}NO$: C, 78.11; H, 7.95; Found: C, 77.60; H, 7.82.

EXAMPLE 5

Synthesis of
2,6-dichloro-3-(pyrrol-1-yl)phenylmethanol as an
intermediate (Route V)

Step A Synthesis of
1-bromomethyl-2,6-dichloro-3-nitrobenzene

A stirred solution of 28.8 grams (0.14 mole) of 2,6-dichloro-3-nitrotoluene in 250 ml of carbon tetrachloride was heated to reflux and 0.1 gram of benzoyl peroxide was added. The reaction mixture was stirred for 10 minutes and 24.9 grams (0.14 mole) of N-bromosuccinimide and an additional 0.1 gram of benzoyl peroxide were added. Upon complete addition the reaction mixture was heated under reflux for 16 hours while being irradiated with a 250 watt white light. The reaction mixture was cooled and a solid precipitate collected by filtration. The solid was washed with carbon tetrachloride. The combined solid and filtrate was washed with 100 ml of an aqueous solution saturated with sodium chloride. The organic layer was dried with magnesium sulfate and the mixture filtered. A small sample of the filtrate was concentrated under reduced pressure to a residual oil. The oil was analyzed by nuclear magnetic resonance spectroscopy, which indicated that the oil was largely unreacted starting materials. The oil was combined with another 24.9 grams (0.14 mole) of N-bromosuccinimide and 0.1 gram of benzoyl peroxide in 250 ml of carbon tetrachloride. The stirred mixture was heated under reflux for 20 hours while being irradiated with a 250 watt white light. The reaction mixture was cooled and worked up as described above to give 32.6 grams of product containing 50% 1-bromomethyl-2,6-dichloro-3-nitrobenzene and 50% 2,6-dichloro-3-nitrotoluene, as an oil. The nmr and the ir spectra were consistent with the proposed structure.

Step B Synthesis of 2,6-dichloro-3-nitrophenylmethyl acetate

A rapidly stirred solution of the mixture from Step A, 20.6 grams (0.21 mole) of potassium acetate and 3.0 grams of tetrabutylammonium bromide in 250 ml of acetonitrile was heated under reflux for 24 hours. The reaction mixture was cooled and filtered. The filtrate was washed with two portions of an aqueous solution saturated with sodium chloride. The organic layer was slurried with magnesium sulfate, decolorizing carbon, and 500 grams of silica gel. The mixture was filtered and the filtrate concentrated under reduced pressure to give 28.7 grams of 50% 2,6-dichloro-3-nitrophenylmethyl acetate and 50% 2,6-dichloro-3-nitrotoluene. The nmr and the ir spectra were consistent with the proposed structure.

Step C Synthesis of a mixture of 3-amino-2,6-dichlorophenylmethanol and 2,4-dichloro-3-methylaniline A stirred mixture of the product of Step B and 47.7 grams (0.854 mole) of iron filings in 200 ml of water was heated to reflux and 100 ml of glacial acetic acid was added dropwise during a one hour period. Upon complete addition the refluxing of the reaction mixture continued for 3.5 hours. The reaction mixture was cooled and 500 ml of toluene was added. The mixture was filtered through filter aid. The filtrate was placed in a separatory funnel and the aqueous layer withdrawn. The filter cake was placed in a beaker and slurried with an additional 500 ml of toluene. The mixture was again filtered. The filtrate was used to once again extract the aqueous layer. The combined toluene layers were washed with 200 ml of an aqueous solution saturated with sodium chloride, then extracted with three portions of 200 ml each of aqueous 2 N hydrochloric acid. The combined extracts were washed with 200 ml of toluene then made basic with aqueous 25% sodium hydroxide solution. The mixture was extracted with three portions of 100 ml each of chloroform. The combined extracts were concentrated under reduced pressure to give 2.7 grams of brown solid. Analysis of the solid by nuclear magnetic resonance spectroscopy indicated the solid to be approximately 57% 3-amino-2,6-dichlorophenylmethanol, the remainder being 2,4-dichloro-3-methylaniline. The mixture was used without further purification.

Step D Synthesis of 2,6-dichloro-3-(pyrrol-1-yl)phenylmethanol

This compound was prepared in the manner of Example 1, Step A using 2.5 grams of the mixture of 3-amino-2,6-dichlorophenylmethanol and 2,4-dichloro-3-methylaniline, 1.7 grams (0.013 mole) of 2,5-dimethoxytetrahydrofuran in 25 ml of glacial acetic acid. The yield was 2.9 grams of a mixture of 2,6-dichloro-3-(pyrrol-1-yl)phenylmethyl acetate, 2,6-dichloro-3-(pyrrol-1-yl)phenylmethanol, and 1-(2,4-dichloro-3-methylphenyl)pyrrole. The product was used without further purification.

Step E Conversion of Step D mixture of 2,6-dichloro-3-(pyrrol-1-yl)phenylmethanol To a stirred solution of 2.0 grams of the mixture from Step D in 25 ml of methanol was added 0.4 gram of solid sodium hydroxide. The mixture was heated under reflux for two hours then poured into water. The mixture was neutralized with aqueous 2 N hydrochloric acid then made basic with aqueous 2 N sodium hydroxide. The mixture was extracted with 100 ml of methylene chloride. The extract was washed with 50 ml of an aqueous solution saturated with sodium chloride then dried with magnesium sulfate. The mixture was filtered and the filtrate concentrated under reduced pressure to a residue. The residue was purified by column chromatography on silica gel. Elution was accomplished with 100% toluene, 10% methylene chloride-toluene, 50% methylene chloride-toluene, 80% methylene chloride-toluene, and 100% methylene chloride. The appropriate fractions were combined to give 1.6 grams of 2,6-dichloro-3-(pyrrol-1-yl)phenylmethanol.

The nmr and the ir spectra were consistent with the proposed structure.

EXAMPLE 6

Synthesis of 2-bromo-3-(pyrrol-1-yl)phenylmethanol as an intermediate (Route VI)

Step A Synthesis of 2-bromo-3-nitrotoluene

A stirred solution of 75.0 grams (0.493 mole) of 2-methyl-6-nitroaniline and 40 ml of aqueous 48% hydrobromic acid in 135 ml of water was cooled to 0° C. and a solution of 36.2 grams (0.510 mole) of sodium nitrate in 60 ml of water was added dropwise during a one hour period. Upon complete addition the mixture was filtered through glass wool into a large dropping funnel. This solution was added dropwise to a second solution of 77.8 grams (0.542 mole) of cuprous bromide in 165 ml of aqueous 48% hydrobromic acid that was being stirred at 15° C. Upon complete addition the reaction mixture was stirred at 15° C. for a few minutes then was allowed to warm to ambient temperature where it stirred for one hour. The reaction mixture stood for 16 hours then was heated to 60° C. where it stirred for two hours. The reaction mixture was subjected to steam distillation. The distillate was extracted with three portions of 150 ml each of methylene chloride. The combined extracts were washed with two portions of 150 ml each of aqueous 2 N sodium hydroxide and five portions of 200 ml each of an aqueous solution saturated with sodium chloride (until the wash was pH-7). The organic layer was dried with magnesium sulfate while being slurried with decolorizing carbon. The mixture was filtered and the filtrate concentrated under reduced pressure to give 6.6 grams of 2-bromo-3-nitrotoluene; mp 36°-41° C. The nmr spectrum was consistent with the proposed structure. The pot residue from the steam distillation was extracted with 400 ml of methylene chloride. The extract was washed with aqueous 2 N sodium hydroxide then with an aqueous solution saturated with sodium chloride (until the salt wash was pH-7). The organic layer was dried with magnesium sulfate and filtered. The filtrate was concentrated under reduced pressure to give 18.0 grams of 2-bromo-3-nitrotoluene, which was combined with the 6.6 grams of above to give a total yield of 24.6 grams.

Step B Synthesis of 2-bromo-1-bromomethyl-3-nitrobenzene

This compound was prepared in the manner of Example 5, Step A, using 21.0 grams (0.097 mole) of 2-bromo-3-nitrotoluene, 17.5 grams (0.097 mole) of N-bromosuccinimide, and 0.4 gram of benzoyl peroxide in 200 ml of carbon tetrachloride. The yield of 2-bromo-1-bromomethyl-3-nitrobenzene was 21.4 grams. The nmr spectrum was consistent with the proposed structure.

Step C Synthesis of 2-bromo-3-nitrophenylmethyl acetate

This compound was prepared in the manner of Example 5, Step B, using 10.7 grams (0.036 mole) of 2-bromo-1-bromomethyl-3-nitrobenzene, 5.3 grams (0.054 mole) of potassium acetate, and 0.8 gram of tetrabutylammonium chloride in 75 ml of acetonitrile. The yield of 2-bromo-3-nitrophenylmethyl acetate was 11.0 grams; mp 60°-63° C.

The nmr spectrum was consistent with the proposed structure.

Step D Synthesis of 3-amino-2-bromophenylmethyl acetate

A mixture of 5.7 grams (0.022 mole) of 2-bromo-3-nitrophenylmethyl acetate, 0.1 gram of platinum oxide and 2.0 ml of morpholine in 200 ml of methanol was hydrogenated using a Parr hydrogenator. The hydrogenation required 2.25 hours. The reaction mixture was filtered and the filtrate concentrated under reduced pressure to give 6.2 grams of 3-amino-2-bromophenylmethyl acetate.

The nmr and the ir spectra were consistent with the proposed structure.

Step E Synthesis of 2-bromo-3-(pyrrol-1-yl)phenylmethyl acetate

This compound was prepared in the manner of Example 1, Step A, using 5.3 grams (0.022 mole) of 3-amino-2-bromophenylmethyl acetate and 3.0 grams (0.023 mole) 2,5-dimethoxytetrahydrofuran in 100 ml of glacial acetic acid. The yield of 2-bromo-3-(pyrrol-1-yl)phenylmethyl acetate was 4.1 grams; mp 84°–86.5° C.

The nmr and the ir spectra were consistent with the proposed structure.

Step F Synthesis of 2-bromo-3-(pyrrol-1-yl)phenylmethanol

This compound was prepared in the manner of Example 5, Step E, using 3.1 grams (0.011 mole) of 2-bromo-3-(pyrrol-1-yl)phenylmethyl acetate and 1.4 grams (0.021 mole) of potassium hydroxide in 25 ml of methanol. The yield of 2-bromo-3-(pyrrol-1-yl)phenylmethanol was 2.5 grams as a white solid; mp 78°–80° C.

The nmr and the ir spectra were consistent with the proposed structure.

EXAMPLE 7

Synthesis of 2,6-difluoro-3-(pyrrol-1-yl)phenylmethanol as an intermediate (Route VII)

Step A Synthesis of 2,6-difluoro-3-nitrobenzoic acid

A mixture of 31.4 grams (0.498 mole) of 70% nitric acid and 107.1 grams (1.092 moles) of concentrated sulfuric acid was cooled to 10° C. and added dropwise to 75.0 grams (0.474 mole) of stirred 2,6-difluorobenzoic acid. The complete addition required 25 minutes during which time the resultant reaction caused the reaction mixture temperature to rise to 50° C. Upon complete addition the reaction mixture temperature was maintained at 50° C. for one hour, then allowed to cool to ambient temperature where it stirred for 16 hours. The reaction mixture was poured into 250 ml of ice-water and stirred until the ice melted. The mixture was poured into a separatory funnel and extracted with three portions of diethyl ether. The combined extracts were washed with three portions of 400 ml of an aqueous solution saturated with sodium chloride. The organic layer was filtered through phase separation paper and the filtrate concentrated under reduced pressure to a residual solid. The solid was recrystallized from heptane-ethyl acetate to give 19.4 grams of 2,6-difluoro-3-nitrobenzoic acid. The mother liquor was concentrated under reduced pressure to give an additional 56.5 grams of this product.

The nmr spectrum was consistent with the proposed structure.

Step B Synthesis of 3-amino-2,6-difluorobenzoic acid

This compound was prepared in the manner of Example 6, Step D, using 10.0 grams (0.049 mole) of 2,6-difluoro-3-nitrobenzoic acid, 0.5 gram of 10% platinum on charcoal, and 2.0 ml of morpholine in 250 ml of methanol. The yield of 3-amino-2,6-difluorobenzoic acid was 11.6 grams as an oil.

The nmr and the ir spectra were consistent with the proposed structure.

Step C Synthesis of 2,6-difluoro-3-(pyrrol-1-yl)benzoic acid

This compound was prepared in the manner of Example 1, Step A, using 8.6 grams (0.049 mole) of 3-amino-2,6-difluorobenzoic acid, and 6.8 grams (0.052 mole) of 2,5-dimethoxytetrahydrofuran in 200 ml of glacial acetic acid. The yield of 2,6-difluoro-3-(pyrrol-1-yl)benzoic acid was 4.3 grams as a solid.

The nmr spectrum was consistent with the proposed structure.

Step D Synthesis of 2,6-difluoro-3-(pyrrol-1-yl)phenylmethanol

This compound was prepared in the manner of Example 2, Step C, using 4.3 grams (0.019 mole) of 2,6-difluoro-3-(pyrrol-1-yl)benzoic acid, and 29 ml of borane-tetrahydrofuran complex in 100 ml of tetrahydrofuran. The yield of 2,6-difluoro-3-(pyrrol-1-yl)phenylmethanol was 1.3 grams; mp <60° C.

The nmr and the ir spectra were consistent with the proposed structure.

The insecticidal esters of this invention are prepared with the foregoing pyrrolylmethanols with an acid halide of a pyrethroid acid, as illustrated in the example below.

EXAMPLE 8

Synthesis of [2-methyl-3-(pyrrol-1-yl)phenyl]methyl cis-3-(2-chloro-3,3,3-trifluoro-1-propenyl)-2,2-dimethylcyclopropanecarboxylate A stirred solution of 2.0 grams (0.011 mole) of 2-methyl-3-(pyrrol-1-yl)phenylmethanol (prepared in Example 2), and 0.9 gram (0.011 mole) of pyridine in 30 ml of toluene was warmed to 50° C. Under a dry-nitrogen atmosphere 2.8 grams (0.011 mole) of cis-3-(2-chloro-3,3,3-trifluoro-1-propenyl)-2,2-dimethylcyclopropanecarbonyl chloride in 2 ml of toluene was added in one portion. The addition caused an exothermic reaction which raised the reaction mixture temperature from 50° C. to 55° C. Upon complete addition the reaction mixture was heated to 60° C. where it was stirred for 2.5 hours. The reaction mixture was cooled and poured into a separatory funnel with 300 ml of heptane. The resultant organic layer was washed with 100 ml of an aqueous solution of 2 N hydrochloric acid then with 200 ml of an aqueous solution of 2 N sodium hydroxide. The organic layer was dried with magnesium sulfate and filtered. The filtrate was concentrated under reduced pressure to a residual oil. The oil was purified by distillation using a Kugelrohr distilling system to give 3.8 grams of [2-methyl-3-(pyrrol-1-yl)phenyl]methyl cis-3-(2-chloro-3,3,3-trifluoro-1-propenyl)-2,2-dimethylcyclopropanecarboxylate, bp 135° C./0.04 mm.

The nmr and the ir spectra were consistent with the proposed structure.

Analysis calc'd for $C_{21}H_{21}ClF_3NO_2$: C, 61.25; H, 5.13; Found: C, 61.33; H, 4.90.

Table I illustrates compounds prepared as illustrated in this example.

In the method aspect of this invention an effective insecticidal, acaricidal amount of the compound is applied to the locus where control is desired, for example, to the insect itself, to the foliage or seeds of agricultural plants, or to surfaces on which the insect feeds. The compounds are useful for the control of household, veterinary, and crop pests and may be applied as technical material or as a formulated product.

Typical formulations include compositions of the active ingredient in combination with an agriculturally acceptable carrier or extender, preferably with a surface-active agent, and optionally with other active ingredients. Suitable formulations include granules, powders, or liquids, the choice varying with the type of pest and environmental factors present at the particular locus of infestation. Thus, the compounds may be formulated as granules of various sizes, as dusts, as wettable powders, as emulsifiable concentrates, as solutions, as dispersions, as controlled release compositions, and the like.

A typical formulation may vary widely in concentration of the active ingredient depending upon the particular agent used, the additives and carriers used, other active ingredients and the desired mode of application. With due consideration of these factors, the active ingredient of a typical formulation may, for example, be suitably present at a concentration of about 0.1% up to about 99.5% by weight of the formulation. An agriculturally acceptable carrier may comprise about 99.9% by weight to as low as about 0.5% by weight of the formulation. Compatible surface-active agents, if employed in the formulation, may be present at various concentrations, suitably in the range of 1% to 30% by weight of the formulation.

The formulation may be used as such or diluted to a desired use dilution with a diluent or carrier suitable for facilitating dispersion of the active ingredients. The concentration of the active ingredient in the use dilution may be in the range of about 0.01 to about 10% by weight. Many variations of spraying, dusting, and controlled or slow release compositions of a type known in the art may be used by substituting or adding a compound of this invention into the compositions known or apparent to the art.

The compounds of this invention may be formulated and applied with other compatible active agents, including nematicides, insecticides, acaricides, fungicides, plant regulators, herbicides, fertilizers, etc.

In applying these compounds, whether alone or with other agricultural chemicals, an effective insecticidal amount of the active ingredient must be applied. While the application rate will vary widely depending on the choice of compound, the formulation and mode of application, the plant species being protected, and the planting density, a suitable use rate may be in the range of 0.005 to 3 kg./hectare, preferably 0.01 to about 1 kg./hectare.

The compounds of this invention were tested for activity against various crop pests as follows:

Topical Application: The compounds of this invention were tested for insecticidal activity against southern armyworm (*Spodoptera eridania*), Mexican bean beetle (*Epilachna varivestis*) and milkweed bug (*Oncopeltus fasciatus*) by applying on the third dorsal thoracic segment of each larvae a one microliter droplet containing 5 mg/ml of test compound in acetone (5000 ng/insect). The test was allowed to stand 24 hours after application and was then read to determine the percent kill. The test results are reported in Table II below. Except for three compounds which were not active against milkweed bug, the compounds all showed high levels of insecticidal activity.

To determine the $LD_{50}$ of the compounds the topical application test was repeated by applying various amounts of toxicant. Also included in this determination were cabbage looper (*Tricoplusia ni*) and tobacco budworm (*Heliothis virescens*). The resulting $LD_{50}$ values are reported in Table II.

Foliar Application: The activity of some of the compounds of the invention against pea aphid (*Acyrthosiphon pisum*) and twospotted spider mite (*Tetranychus urticae*) was determined by foliar application of the test compound. The test materials were formulated as aqueous solutions containing acetone and a few drops of acetylphenoxypolyethoxyethanol. Activity against pea aphid was determined on English fava bean plants the leaves of which were sprayed to runoff with various concentrations of test solution prior to infestation with adult aphids. Activity against twospotted spider mite was evaluated on pinto bean plants whose leaves were sprayed to runoff with various concentrations of test solution after infestation with adult mites. Mortality was read approximately 48 hours after treatment. The results are reported in Table II.

TABLE 1A

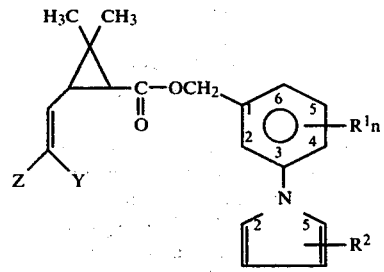

| Cpd No. | Y | Z | R¹ | R² | Isomer | Empirical Formula/ Elemental Analysis | MP/BP |
|---|---|---|---|---|---|---|---|
| 1 | Cl | Cl | H | H | c | $C_{19}H_{19}Cl_2NO_2$ Calc'd: C 62.69; H 5.26; Found: C 62.45; H 5.56. | — |

TABLE 1A-continued

Structure: cyclopropane with gem-dimethyl, C(=O)-OCH2-phenyl (positions 1-6) with R^1_n, and N-pyrrole (positions 2-5) with R^2; vinyl substituent with Y, Z.

| Cpd No. | Y | Z | R$^1$ | R$^2$ | Isomer | Empirical Formula/ Elemental Analysis | MP/BP |
|---|---|---|---|---|---|---|---|
| 2 | Cl | Cl | 2-CH$_3$ | H | c | C$_{20}$H$_{21}$Cl$_2$NO$_2$<br>Calc'd: C 62.31; H 5.77;<br>Found: C 63.50; H 5.59. | 138° C. ± 3° C./<br>0.05 mm |
| 3 | Cl | Cl | 2-CH$_3$ | H | t | C$_{20}$H$_{21}$Cl$_2$NO$_2$<br>Calc'd: C 62.31; H 5.77;<br>Found: C 64.45; H 5.57. | 145° C./<br>0.05 mm |
| 4 | CF$_3$ | Cl | 2-CH$_3$ | H | c | C$_{21}$H$_{21}$ClF$_3$NO$_2$<br>Calc'd: C 61.25; H 5.13;<br>Found: C 61.33; H 4.90. | 135° C./<br>0.04 mm |
| 5 | Br | Br | 2-CH$_3$ | H | c | C$_{20}$H$_{21}$Br$_2$NO$_2$<br>Calc'd: C 51.42; H 4.53;<br>Found: C 51.67; H 4.39. | — |
| 6 | Cl | Cl | H | 2,5-di-CH$_3$ | c | C$_{21}$H$_{13}$Cl$_2$NO$_2$<br>Calc'd: C 64.29; H 5.90;<br>Found: C 63.82; H 5.75. | — |
| 7 | CF$_3$ | Cl | H | 2,5-di-CH$_3$ | c | C$_{22}$H$_{23}$ClF$_3$NO$_2$<br>Calc'd: C 62.05; H 5.44;<br>Found: C 62.40; H 5.12. | — |
| 8 | CF$_3$ | Cl | 2-CH$_3$ | 2,5-di-CH$_3$ | c | C$_{23}$H$_{25}$ClF$_3$NO$_2$<br>Calc'd: C 62.80; H 5.72;<br>Found: C 62.18; H 5.12. | — |
| 9 | Cl | Cl | 2-CH$_3$ | 2,5-di-CH$_3$ | c | C$_{22}$H$_{25}$Cl$_2$NO$_2$<br>Calc'd: C 65.03; H 6.20;<br>Found: C 64.55; H 5.92. | — |
| 10 | Cl | Cl | 2-CH$_3$ | 2,5-di-CH$_3$ | t | C$_{22}$H$_{25}$Cl$_2$NO$_2$<br>Calc'd: C 65.03; H 6.20;<br>Found: C 65.40; H 6.18. | — |
| 11 | Cl | Cl | 2,6-di-Cl | H | c | C$_{19}$H$_{17}$Cl$_4$NO$_2$<br>Calc'd: C 52.68; H 3.96;<br>Found: C 53.66; H 4.50. | — |
| 12 | CF$_3$ | Cl | 2,6-di-Cl | H | 1R,c | C$_{20}$H$_{17}$Cl$_3$F$_3$NO$_2$<br>Calc'd: C 51.47; H 3.67;<br>Found: C 53.62; H 4.24. | — |
| 13 | Cl | Cl | 2,6-di-Cl | H |  | C$_{19}$H$_{17}$Cl$_4$NO$_2$<br>Calc'd: C 52.68; H 3.96;<br>Found: C 52.79; H 3.89. | — |
| 14 | Cl | Cl | 2-CH$_3$ | H | 1R,c | C$_{19}$H$_{21}$Cl$_2$NO$_2$<br>Calc'd: C 62.31; H 5.77;<br>Found: C 63.59; H 5.89. | 145° C./<br>0.05 mm |
| 15 | CH$_3$ | CH$_3$ | 2-CH$_3$ | H | t | C$_{22}$H$_{27}$NO$_2$<br>Calc'd: C 78.31; H 8.06;<br>Found: C 77.82; H 8.13. | — |
| 16 | Br | Br | 2-CH$_3$ | H | t | C$_{20}$H$_{21}$Br$_2$NO$_3$<br>Calc'd: C 51.42; H 4.53;<br>Found: C 51.29; H 4.75. | — |
| 17 | CF$_3$ | Cl | 2-Br | H | c | C$_{20}$H$_{18}$BrClF$_3$NO$_2$<br>Calc'd: C 50.39; H 3.81;<br>Found: C 50.39; H 3.81. | — |
| 18 | Cl | Cl | 2-Br | H | c | C$_{19}$H$_{18}$BrClNO$_2$<br>Calc'd: C 51.49; H 4.09;<br>Found: C 51.32; H 4.10. | — |
| 19 | Cl | Cl | 2-Br | H | t | C$_{19}$H$_{18}$BrCl$_2$NO$_2$<br>Calc'd: C 51.49; H 4.09;<br>Found: C 51.60; H 4.42. | — |
| 20 | Cl | Cl | 2,6-di-F | H | c/t | C$_{19}$H$_{17}$Cl$_2$F$_2$NO$_2$<br>Calc'd: C 57.01; H 4.28;<br>Found: C 57.51; H 4.46. | — |
| 21 | Cl | Cl | 2,6-di-F | H |  | C$_{19}$H$_{17}$Cl$_2$F$_2$NO$_2$<br>Calc'd: C 57.01; H 4.28;<br>Found: C 57.39; H 4.29. | — |
| 22 | CF$_3$ | Cl | 2,6-di-F | H |  | C$_{20}$H$_{17}$ClF$_5$NO$_2$<br>Calc'd: C 55.37; H 3.95;<br>Found: C 55.97; H 4.30. | — |
| 23 | CF$_3$ | Cl | 6-CH$_3$ | H | c | C$_{21}$H$_{21}$ClF$_3$NO$_2$<br>Calc'd: C 61.25; H 5.13;<br>Found: C 61.33; H 5.17. | 152° C./<br>0.04 mm |

TABLE 1A-continued

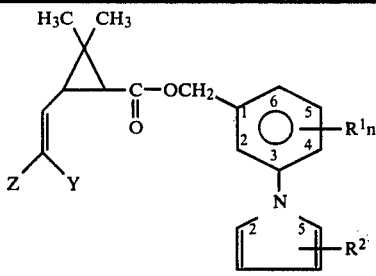

| Cpd No. | Y | Z | R¹ | R² | Isomer | Empirical Formula/ Elemental Analysis | MP/BP |
|---|---|---|---|---|---|---|---|
| 24 | Cl | Cl | 6-CH$_3$ | H | c/t | C$_{20}$H$_{21}$Cl$_2$NO$_2$<br>Calc'd: C 63.50; H 5.59<br>Found: C 64.01; H 6.10. | 162° C./<br>0.05 mm |
| 25 | Cl | Cl | 6-CH$_3$ | H | c | C$_{20}$H$_{21}$Cl$_2$NO$_2$<br>Calc'd: C 63.50; H 5.59;<br>Found: C 64.04; H 5.30 | 162° C./<br>0.05 mm |
| 26 | CF$_3$ | Cl | 2,5-di-Cl | H | c | C$_{20}$H$_{17}$Cl$_3$F$_3$NO$_2$<br>Calc'd: C 51.47; H 3.67;<br>Found: C 51.43; H 3.69. | |

TABLE 1B

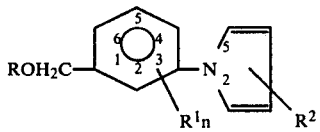

| Cpd No. | R | R¹ | R² | Isomer | Empirical Formula/ Elemental Analysis | MP/BP |
|---|---|---|---|---|---|---|
| 27 | (pivaloyl group) | 2-CH$_3$ | H | | C$_{20}$H$_{25}$NO$_2$<br>Calc'd: C 77.14; H 8.08;<br>Found: C 76.69; H 7.94. | 48-49° C. |
| 28 | 4-Cl-C$_6$H$_4$-CH(iPr)-C(O)- | 2-CH$_3$ | H | | C$_{23}$H$_{24}$ClNO$_2$<br>Calc'd: C 72.34; H 6.33;<br>Found: C 72.27; H 5.99. | 155° C./<br>0.05 mm |
| 29 | (cyclopentylidene dimethylcyclopropanecarbonyl) | 2-CH$_3$ | H | 1R,t | C$_{24}$H$_{29}$NO$_2$<br>Calc'd: C 79.31; H 8.03;<br>Found: C 79.29; H 7.69. | 160° C./<br>0.05 mm |
| 30 | (4-OEt-phenyl)-CH(H)-C(Cl$_2$)(H)-C(O)- | 2-CH$_3$ | H | | C$_{24}$H$_{23}$NO$_3$<br>Calc'd: C 64.87; H 5.22;<br>Found: C 65.95; H 5.54. | |

TABLE 2

| | | Topical Application | | |
|---|---|---|---|---|
| Cpd No. | Insect Species* | Percent Kill at 5000 ng/insect | LD$_{50}$ ng/insect | Foliar % Kill at (ppm) |
| 1 | SAW | 100 | 246 | |
| | MBB | 100 | 240 | |
| | MWB | 100 | 1392 | |
| | TSM | | | 10(64) |
| 2 | SAW | 100 | 55 | |
| | MBB | 100 | 30 | |
| | MWB | 100 | 201 | |
| | TBW | | 47 | |
| | CL | | 65 | |
| | PA | | | 100(16) |
| | TSM | | | 92(500) |
| 3 | SAW | 100 | 266 | |
| | MBB | 100 | 98 | |
| | MWB | 100 | 158 | |
| | PA | | | 100(500) |
| 4 | SAW | 100 | 11 | |
| | MBB | 100 | 19 | |
| | MWB | 100 | 195 | |
| | TBW | | 14 | |
| | CL | | 29 | |
| | PA | | | 90(16) |
| | TSM | | | 66(20) |

TABLE 2-continued

| Cpd No. | Insect Species* | Topical Application Percent Kill at 5000 ng/insect | LD50 ng/insect | Foliar % Kill at (ppm) |
|---|---|---|---|---|
| 5 | SAW | 100 | 65 | |
| | MBB | 100 | 3 | |
| | MWB | 100 | 300 | |
| | CL | | 48 | |
| | TBW | | 48 | |
| | PA | | | 65(16) |
| 6 | SAW | 100 | 728 | |
| | MBB | 100 | 283 | |
| | MWB | 0 | | |
| 7 | SAW | 100 | 541 | |
| | MBB | 100 | 388 | |
| | MWB | 20 | | |
| 8 | SAW | 100 | 2650 | |
| | MBB | 100 | 275 | |
| | MWB | 55 | | |
| 9 | SAW | 100 | 2371 | |
| | MBB | 100 | 441 | |
| | MWB | 0 | | |
| 10 | SAW | 30 | | |
| | MBB | 90 | 4183 | |
| | MWB | 0 | | |
| | PA | | | 100(500) |
| | TSM | | | 0(500) |
| 11 | SAW | 100 | 62 | |
| | MBB | 100 | 211 | |
| | MWB | 100 | 858 | |
| | CL | | 132 | |
| | TBW | | | |
| | PA | | | 100(500) |
| | TSM | | | 100(500) |
| 12 | SAW | 100 | 29 | |
| | MBB | 100 | 27 | |
| | MWB | 100 | 370 | |
| | CL | | 96 | |
| | TBW | | 31 | |
| | PA | | | 100(500) |
| | TSM | | | 100(500) |
| 13 | SAW | 100 | 18 | |
| | MBB | 100 | 30 | |
| | MWB | 100 | 395 | |
| | CL | | 69 | |
| | TBW | | 32 | |
| | PA | | | 100(500) |
| | TSM | | | 100(500) |
| 14 | SAW | 100 | 29 | |
| | MBB | 100 | 28 | |
| | MWB | 100 | 89 | |
| | TBW | | 13 | |
| | CL | | 34 | |
| | PA | | | 100(500) |
| | TSM | | | 100(500) |
| 15 | SAW | 100 | 948 | |
| | MBB | 90 | 214 | |
| | MWB | 100 | 697 | |
| 16 | SAW | 100 | 392 | |
| | MBB | 100 | 42 | |
| | MWB | 100 | 214 | |
| 17 | SAW | 100 | 57 | |
| | MBB | 100 | 23 | |
| | MWB | 100 | 306 | |
| | TBW | | 38 | |
| | CL | | 91 | |
| 18 | SAW | 100 | 205 | |
| | MBB | 100 | 58 | |
| | MWB | 100 | 460 | |
| | PA | | | 100(500) |
| | TSM | | | 0(500) |
| 19 | SAW | 100 | 765 | |
| | MBB | 100 | 74 | |
| | MWB | 100 | 299 | |
| 20 | SAW | 100 | 90 | |
| | MBB | 100 | 131 | |
| | MWB | 100 | 423 | |
| | CL | | 237 | |
| | TBW | | 105 | |
| 21 | SAW | 100 | 50 | |
| | MBB | 100 | 93 | |
| | MWB | 100 | 517 | |
| | CL | | 309 | |
| | TBW | | 76 | |
| 22 | SAW | 100 | 35 | |
| | MBB | 100 | 47 | |
| | MWB | 100 | 252 | |
| | CL | | 166 | |
| | TBW | | 27 | |
| 23 | SAW | 100 | 280 | |
| | MBB | 100 | 325 | |
| | MWB | 100 | 664 | |
| | PA | | | 95(500) |
| | TSM | | | 0(500) |
| 24 | SAW | 100 | 638 | |
| | MBB | 100 | 909 | |
| | MWB | 100 | 2381 | |
| | PA | | | 100(500) |
| | TSM | | | 0(500) |
| 25 | SAW | 100 | 379 | |
| | MBB | 100 | 1057 | |
| | MWB | 20 | | |
| | PA | | | 90(500) |
| | TSM | | | 0(500) |
| 26 | SAW | 100 | 344 | |
| | MBB | 100 | 260 | |
| | MWB | 25 | | |
| | PA | | | 50(500) |
| | TSM | | | 0(500) |
| 27 | SAW | 100 | 435 | |
| | MBB | 100 | 113 | |
| | MWB | 100 | 737 | |
| | PA | | | 85(500) |
| | TSM | | | 100(500) |
| 28 | SAW | 20 | | |
| | MBB | 100 | 293 | |
| | MWB | 100 | 4399 | |
| 29 | SAW | 100 | 152 | |
| | MBB | 100 | 42 | |
| | MWB | 100 | 64 | |
| | CL | | 95 | |
| | TBW | | 103 | |
| | PA | | | 70(64) |
| | TSM | | | 25(64) |
| 30 | SAW | 100 | 599 | |
| | MWB | 35 | | |
| | PA | | | 100(500) |
| | TSM | | | 0(500) |

*SAW - Southern armyworm
MBB - Mexican bean beetle
MWB - Milkweed bug
TBW - Tobacco budworm
CL - Cabbage looper
PA - Pea aphid
TSM - Twospotted spider mite

I claim:
1. A compound of the formula

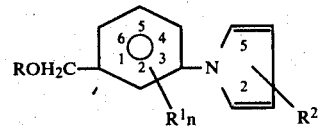

in which $R^1$ is halogen or lower alkyl, n is 0, 1 or 2, $R^2$ is hydrogen or 2,5-dimethyl and R is 2,2,3,3-tetramethylcyclopropylcarbonyl, 1-(4-chlorophenyl)-2-methylpropyl-1-carbonyl, 1-(4-ethoxyphenyl)-2,2-dichlorocyclopropylcarbonyl, or a cyclopropanecarboxylic acid residue of the formula

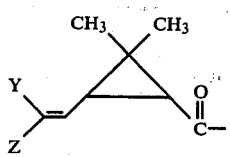

wherein Y and Z are independently halogen, lower alkyl, perhaloalkyl of 1 or 2 carbon atoms, or are joined to form a cyclopentylidene group.

2. The compound of claim 1 wherein n is 0, $R^1$ is 2-lower alkyl or 2-halo and n is 1, or $R^1$ is halogen or lower alkyl at the 2 and 6 positions of the phenyl ring and n is 2.

3. The compound of claim 2 in which $R^1$ is bromine, chlorine, fluorine or methyl, n is 1 or 2, $R^2$ is hydrogen and R is an acid residue of the formula

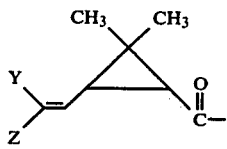

in which Y and Z are each halogen, or one of Y and Z is halogen and the other of Y and Z is trifluoromethyl, or Y and Z form a cyclopentylidene ring.

4. The compound of claim 3, [2-methyl-3-(pyrrol-1-yl)phenyl]methyl 3-(2-chloro-3,3,3-trifluoro-1-propenyl)-2,2-dimethylcyclopropanecarboxylate.

5. The compound of claim 3, [2-methyl-3-(pyrrol-1-yl)phenyl]methyl 3-(2,2-dibromoethenyl)-2,2-dimethylcyclopropanecarboxylate.

6. The compound of claim 3, [2-methyl-3-(pyrrol-1-yl)phenyl]methyl 3-(2,2-dichloroethenyl)-2,2-dimethylcyclopropanecarboxylate.

7. The compound of claim 3, [2-bromo-3-(pyrrol-1-yl)phenyl]methyl 3-(2-chloro-3,3,3-trifluoro-1-propenyl)-2,2-dimethylcyclopropanecarboxylate.

8. The compound of claim 3, [2,6-difluoro-3-(pyrrol-1-yl)phenyl]methyl 3-(2,2-dichloroethenyl)-2,2-dimethylcyclopropanecarboxylate.

9. The compound of claim 3, [2,6-difluoro-3-(pyrrol-1-yl)phenyl]methyl 3-(2-chloro-3,3,3-trifluoro-1-propenyl)-2,2-dimethylcyclopropanecarboxylate.

10. The compound of claim 3, [2-methyl-3-(pyrrol-1-yl)phenyl]methyl 3-(cyclopentylidinemethyl)-2,2-dimethylcyclopropanecarboxylate.

11. A method for controlling insects or acarids which comprises applying to a locus where control is desired an insecticidal or a acaricidal amount of a compound of claim 1, 2, 3, 4, 5, 6, 7, 8, 9 or 10 in which R is other than hydrogen.

12. An insecticidal or acaricidal composition comprising an insecticidal or acaricidal amount of a compound of claim 1, 2, 3, 4, 5, 6, 7, 8, 9, or 10, in which R is other than hydrogen, in admixture with a compatible adjuvant, diluent or carrier.

* * * * *